(12) United States Patent
Ghuge

(10) Patent No.: US 11,484,435 B2
(45) Date of Patent: Nov. 1, 2022

(54) DYNAMIC MANDIBULAR AND LINGUAL REPOSITIONING DEVICES, CONTROLLER STATION, AND METHODS OF TREATING AND/OR DIAGNOSING MEDICAL DISORDERS

(71) Applicant: Raghavendra Vitthalrao Ghuge, Tyler, TX (US)

(72) Inventor: Raghavendra Vitthalrao Ghuge, Tyler, TX (US)

( * ) Notice: Subject to any disclaimer, the term of this patent is extended or adjusted under 35 U.S.C. 154(b) by 119 days.

(21) Appl. No.: 16/784,750

(22) Filed: Feb. 7, 2020

(65) Prior Publication Data

US 2021/0145627 A1    May 20, 2021

Related U.S. Application Data

(60) Provisional application No. 62/936,032, filed on Nov. 15, 2019.

(51) Int. Cl.
*A61F 5/56* (2006.01)
*A61B 5/00* (2006.01)
(Continued)

(52) U.S. Cl.
CPC ............ *A61F 5/566* (2013.01); *A61B 5/0205* (2013.01); *A61B 5/4836* (2013.01); *A61B 5/682* (2013.01);
(Continued)

(58) Field of Classification Search
CPC ...... A61F 5/566; A61F 2005/563; A61F 5/56; A63B 71/085; A61B 5/4557; A61B 5/4818; A61B 5/682; A61C 7/08
(Continued)

(56) References Cited

U.S. PATENT DOCUMENTS 5,826,579 A    10/1998    Remmers et al.
6,536,439 B1    3/2003    Palmisano
(Continued)

FOREIGN PATENT DOCUMENTS

WO    WO-2017149523 A1 *    9/2017    ............. A61C 5/007
WO    WO-2018123602 A1 *    7/2018    ............. A61F 5/566

OTHER PUBLICATIONS

US 10,350,107, 07/2019, Align Technology Inc. (withdrawn)
(Continued)

*Primary Examiner* — Keri J Nelson
(74) *Attorney, Agent, or Firm* — FisherBroyles, LLP; Susan M. Oiler

(57) ABSTRACT

Mandibular repositioning devices have a mandibular piece having a first teeth covering and having a housing proximate each of a left molar portion and a right molar portion, a protrusive flange extending cranially from each housing, and a maxillary piece having a second teeth covering and having a housing proximate each of a left molar portion and a right molar portion. Each housing encloses a power source electrically connected an on-board circuit board and the housings of the maxillary piece further have the power source electrically connected to a motor operatively connected to a drive for anterior and posterior movements of the mandibular piece. The maxillary piece sits on the mandibular piece with the driver operatively engaged with the protrusive flange. The protrusive flange has a concavely-shaped anterior surface mated to a convexly-shaped head of the driver shaped to match the concavely-shaped anterior surface of the protrusive flange.

21 Claims, 6 Drawing Sheets

(51) Int. Cl.
*A61B 5/0205* (2006.01)
*A61N 1/02* (2006.01)
*A61N 1/05* (2006.01)
*A61N 1/08* (2006.01)
*A61N 1/36* (2006.01)
*A61B 5/1455* (2006.01)
*A61B 5/087* (2006.01)
*A61B 8/08* (2006.01)
*A61B 8/13* (2006.01)
*A61B 5/021* (2006.01)
*A61B 5/024* (2006.01)
*A61B 5/145* (2006.01)

(52) U.S. Cl.
CPC .............. *A61B 5/742* (2013.01); *A61N 1/025* (2013.01); *A61N 1/0548* (2013.01); *A61N 1/08* (2013.01); *A61N 1/3601* (2013.01); *A61B 5/021* (2013.01); *A61B 5/02125* (2013.01); *A61B 5/02438* (2013.01); *A61B 5/087* (2013.01); *A61B 5/14539* (2013.01); *A61B 5/14551* (2013.01); *A61B 5/14552* (2013.01); *A61B 5/4557* (2013.01); *A61B 5/4818* (2013.01); *A61B 8/0883* (2013.01); *A61B 8/13* (2013.01); *A61B 8/483* (2013.01); *A61B 8/486* (2013.01); *A61B 8/488* (2013.01); *A61B 2560/0214* (2013.01); *A61F 2005/563* (2013.01)

(58) Field of Classification Search
USPC .................................................. 128/848, 861
See application file for complete search history.

(56) References Cited

U.S. PATENT DOCUMENTS

| | | |
|---|---|---|
| 6,604,527 B1 | 8/2003 | Palmisano |
| 7,942,824 B1 | 5/2011 | Kayyali et al. |
| 8,355,769 B2 | 1/2013 | Levendowski et al. |
| 10,265,013 B2 | 4/2019 | Lim |
| 10,265,213 B2* | 4/2019 | Shim ........................ A61C 7/36 |
| 2011/0168187 A1* | 7/2011 | Nelissen ................ A61F 5/566 |
| | | 128/848 |
| 2012/0240941 A1 | 9/2012 | Rosenman et al. |
| 2014/0134561 A1 | 5/2014 | Smith et al. |
| 2015/0157491 A1* | 6/2015 | Hofmann ................ A61F 5/566 |
| | | 128/848 |
| 2015/0182374 A1 | 7/2015 | Stenberg et al. |
| 2016/0324681 A1* | 11/2016 | Flanagan ............... A61B 5/682 |
| 2017/0128721 A1 | 5/2017 | Martin et al. |
| 2018/0360646 A1 | 12/2018 | Bedford |
| 2018/0368766 A1 | 12/2018 | Keels |
| 2019/0091061 A1 | 3/2019 | Radmand |
| 2019/0110746 A1 | 4/2019 | Dau et al. |
| 2019/0183670 A1* | 6/2019 | Nagai ..................... A61F 5/566 |
| 2019/0350749 A1 | 11/2019 | Winter et al. |
| 2020/0093435 A1 | 3/2020 | Masri et al. |
| 2020/0375528 A1* | 12/2020 | Flanagan ............... A61B 5/682 |

OTHER PUBLICATIONS

Lennon, "New test could cause OSA's treatment success rate to rise", Chest Physician, MDedge News, Aug. 14, 2017, 4 pages http://www.mdedge.com/chestphysician/article/144587/pulmonology/new-test-could-cause-osas-treatment-success-rate-rise.

Kastoer et al., "The Use of Remotely Controlled Mandibular Positioner as a Predictive Screening Tool for Mandibular Advancement Device Therapy in Patients with Obstructive Sleep Apnea through Single-Night Progressive Titration of the Mandible: A Systematic Review", Journal of Clinical Sleep Medicine, Aug. 2016, 12(10):1411-1421.

PCT/US/2020/060625, International Search Report and Written Opinion, dated Mar. 4, 2021 (13 pages).

Tangent of a Circle, http://byjus.com/maths/tangent-of-a-circle/, Jan. 6, 2016.

* cited by examiner

DYNAMIC MANDIBULAR AND LINGUAL REPOSITIONING DEVICES, CONTROLLER STATION, AND METHODS OF TREATING AND/OR DIAGNOSING MEDICAL DISORDERS

RELATED APPLICATIONS

This application claims the benefit of U.S. Provisional Patent Application No. 62/936,032, filed Nov. 15, 2019, the entirety of which is incorporated herein by reference.

TECHNICAL FIELD

This application relates to mandibular and lingual repositioning devices and methods of treating and/or diagnosing obstructive sleep apnea and other sleep disorders and/or medical conditions using the same, more particularly, to a mandibular and lingual repositioning device that can make protrusive movement and vertical movement of the jaw(s) and provide electrical impulse stimulation to the muscle of the tongue for forward movement of the tongue, simultaneously, sequentially, or independently.

BACKGROUND

Many individuals suffer from disordered breathing while asleep. Some example disorders include obstructive sleep apnea (OSA), snoring, snore arousals, sleep-related hypoxia, and other conditions dependent on, correlated with, and caused by snoring or OSA. OSA is a condition in which sleep is repeatedly interrupted by an inability to breathe, which is typically a results of intermittent obstruction of the airway by the tongue and a general relaxation of the muscles which stabilize the upper airway segment, which can cause a lack of oxygen, snoring, cardiovascular and neurological complications, such as sleep-induced hypertension, heart attacks, cardiac arrhythmias, strokes, Alzheimer's disease, diabetes, weight gain, and depression to name a few.

Mandibular repositioning devices have been FDA-approved and used as a treatment for sleep apnea when treatment by a CPAP (Continuous Positive Airway Pressure) machine has been ineffective for the particular patient, or when a patient is unable to tolerate a PAP (Positive Airway Pressure) device. Most oral appliances on the market have only been able to control approximately 50% of sleep apnea events. There are a large number of patients that are intolerant to PAP devices, some due to the PAP device or the mask but most due to excessive high air pressure that may be medically recommended for keeping an open airway. Repeated adjustments have to be performed in attempts to make intolerant patients tolerate a PAP device, most of which require manual adjustments by a professional or require repeated sleep studies after a sleep study. Since a large number of patients with OSA have thus remained untreated due to various reasons, there is a serious need for a new method of treatment that can maintain an open airway during sleep using a combination of jaw stabilization and simultaneous advancement of the jaw and tongue, i.e., a dynamic mandibular and lingual repositioning device as disclosed herein. There is also a need for such a device that can continuously learn (artificial intelligence) a particular persons sleep-related breathing, blood pressure, heart rate and rhythm, body positioning, depth of sleep and oxygen levels, silent or symptomatic acid reflux during sleep and amount of bruxism (teeth grinding) over periods of days, months and even years while the person sleeps at home or elsewhere, thereby removing the need of performing expensive sleep studies. While using such a device it should lend itself to continuously making automatic, guided, algorithmic (SERVO) adjustments to the treatment of these medical conditions and continuously providing information related to improvement in oxygen levels, breathing, blood pressure, heart rate and rhythm, acid reflux and bruxism and sleep depth, quantity and quality to the controller, cloud-based server system and to the treating physician, providing a lifelong (life of the device) safe open airway with reliable normalization of oxygen, breathing and sleep.

SUMMARY

In all aspects, mandibular repositioning devices have a mandibular piece having a first teeth covering and having a housing proximate each of a left molar portion and a right molar portion, a protrusive flange extending cranially from each housing, and a maxillary piece having a second teeth covering and having a housing proximate each of a left molar portion and a right molar portion. Each housing encloses a power source electrically connected an on-board circuit board and the housings of the maxillary piece further have the power source electrically connected to a motor operatively connected to a drive for anterior and posterior movements of the mandibular piece. The maxillary piece sits on the mandibular piece with the driver operatively engaged with the protrusive flange. The protrusive flange has a concavely-shaped anterior surface mated to a convexly-shaped head of the driver shaped to match the concavely-shaped anterior surface of the protrusive flange.

In some example embodiments, the protrusive flange is releasably attachable to the housing of the mandibular piece.

In all aspects, each power source is a rechargeable battery and each housing has a charging member in an exterior surface thereof. Each on-board circuit board includes a receiver, a transmitter, and a microprocessor having instructions to activate the motors simultaneously linearly translate the driver.

In all aspects, the protrusive flange has a midpoint between opposing ends, and the concavely-shaped anterior surface thereof is an arc of a circle having its center at the temporomandibular joint of the user and a radius terminating at the midpoint or offset above or below the midpoint and defines an angle $\theta_1$ relative to a free end of the opposing ends and defines an angle $\theta_2$ relative to an opposing end. The midpoint is approximately at a point where the mandible is open at about 13 degrees. In one embodiment, $\theta_1$ and $\theta_2$ are in a range of 12 to 15 degrees. In another embodiment, $\theta_1$ and $\theta_2$ are a combination of angle values that sum to 30 degrees, and typically $\theta_2$ is different than $\theta_1$, and $\theta_1$ may be greater than $\theta_2$.

In another aspect, mandibular repositioning devices have a mandibular piece having a first teeth covering and having a housing proximate each of a left molar portion and a right molar portion, wherein each housing encloses a power source electrically connected to an on-board circuit board and to a motor, and a first driver oriented to move caudally and cranially, and a maxillary piece having a second teeth covering. The maxillary piece sits on the mandibular piece with the first driver operatively engaged with the maxillary piece to open or close the mouth of the user.

In all aspects, the mandibular piece has a protrusive flange extending cranially from each housing, and the maxillary piece has a housing proximate each of a left molar portion and a right molar portion thereof. Each housing of the maxillary piece encloses a power source electrically connected to a motor and to a circuit board and has a second driver operatively connected to the motor and in operative engagement with the protrusive flange for anterior and posterior movements of the mandibular piece. The protrusive flange can be releasably attachable to the housing of the mandibular piece In one embodiment, the protrusive flange has a concavely-shaped anterior surface mated to the second driver, and the second driver has a convexly-shaped head to match the shape of the concavely-shaped anterior surface of the protrusive flange.

In another embodiment, the protrusive flange has a bend that orients the free end thereof generally toward the posterior and the second driver has a head shaped to fit the shape of the posterior side of the protrusive flange.

In all aspects, each power source is a rechargeable battery and each housing has a charging member in an exterior surface thereof.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present system.

DETAILED DESCRIPTION

Figure 1:
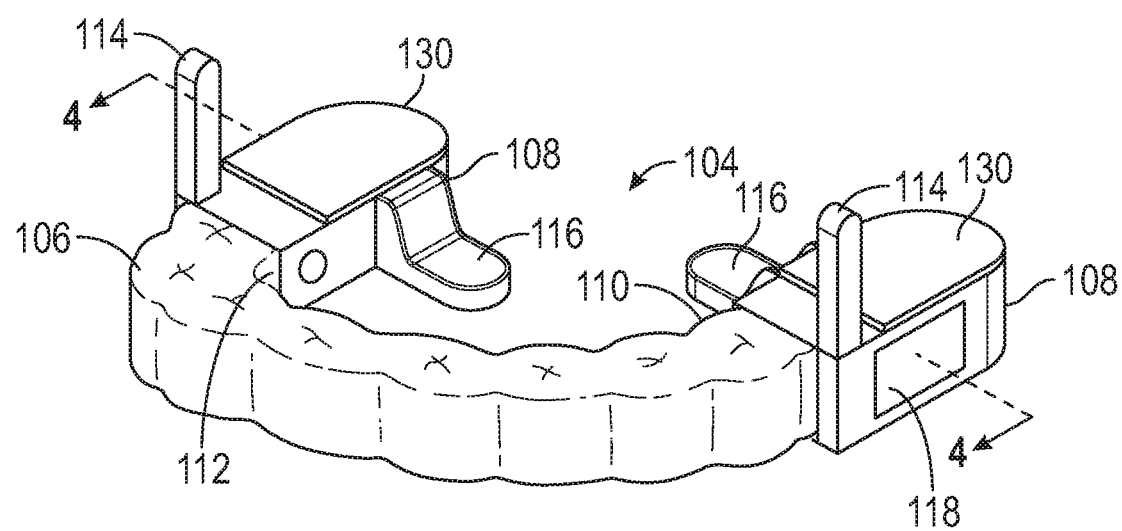
FIG. 1 is a left-side view of a first embodiment of a mandibular lingual repositioning device.

The following detailed description will illustrate the general principles of the invention, examples of which are additionally illustrated in the accompanying drawings. In the drawings, like reference numbers indicate identical or functionally similar elements.

Figure 2:
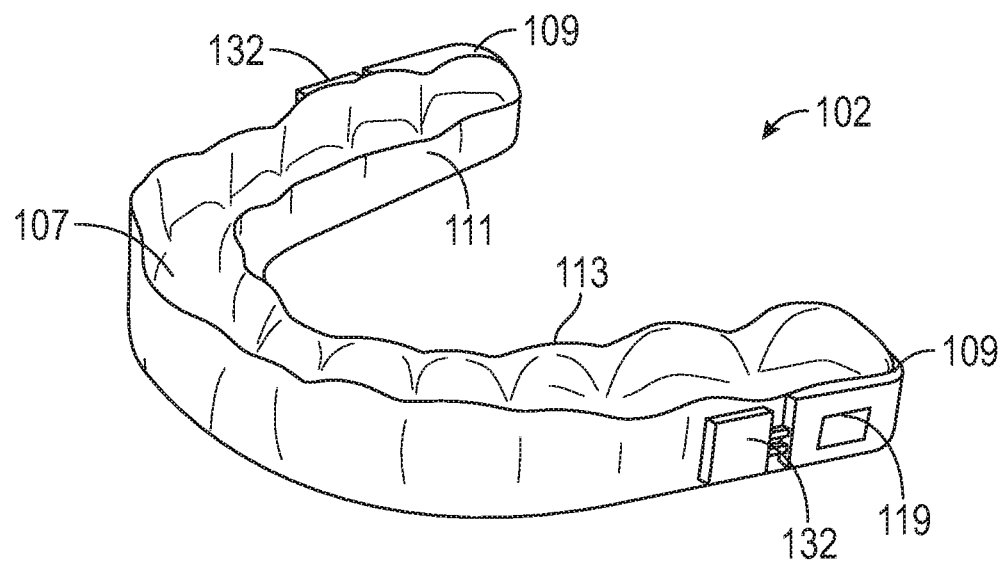
FIG. 2 is a side, perspective view of the mandibular piece of the mandibular lingual repositioning device of FIG. 1.
Figure 3:
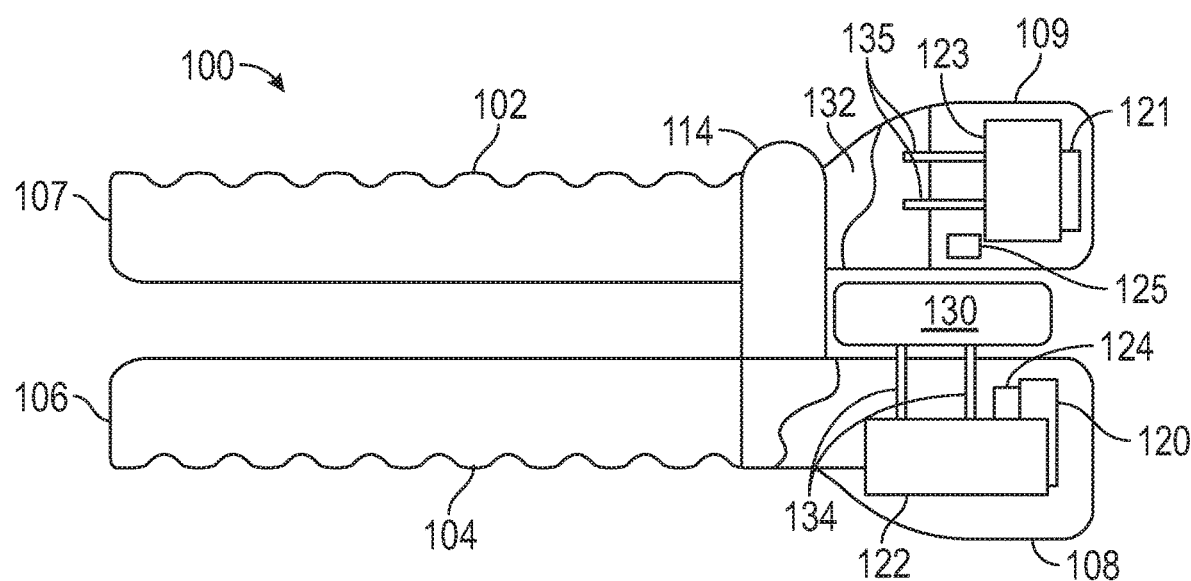
FIG. 3 is a side, perspective view of the maxillary piece as it articulates and fits with the mandibular lingual repositioning device of FIG. 1.

Referring now to FIGS. 1 to 4, a mandibular lingual repositioning device (MLRD) that is dynamic in its movement of the jaw(s) and tongue is represented collectively in FIG. 3 by reference number 100. The MLRD 100 has a maxillary piece 102 seated on a mandibular piece 104 for operative communication of drivers built therein.

Figure 4:
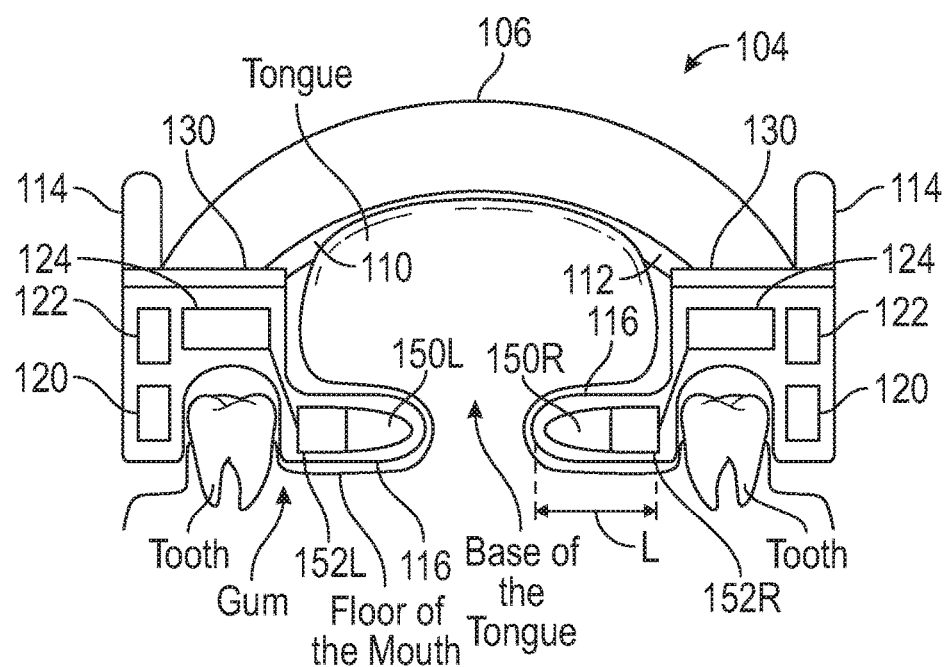
FIG. 4 is a cross-sectional view of the mandibular lingual repositioning device along line 4-4 in FIG. 1.

Turning to FIGS. 1 and 4, the mandibular piece 104 is shown, which has a first teeth covering 106 and has a housing 108 proximate each of a left molar portion 110 and a right molar portion 112. A protrusive flange 114 extends cranially from each housing 108, and a stimulator 116 extends from each housing 108 toward the tongue at a position to lie under the tongue in contact with lingual muscles, in particular the Genioglossus (GG), the Geniohyoid (GH), sub-mentalis (SM), and Glossopharyngeal (GP). The stimulator portion 116 of each housing 108 should be fitted to the user/custom made for the user to ensure proper contact with the lingual muscles. Each stimulator portion 116 while appearing somewhat boxy-looking in the drawings, is more preferably molded of moldable material suitable for use in a human oral cavity and has smooth transitions to its shape and is shaped to match the shape of the user's mouth, especially to sit under the tongue in contact with the base of the tong and the floor of the mouth as shown in FIG. 4. The moldable material may be any of those commercially available or hereinafter developed for use in a human oral cavity.

Referring now to the transverse cross-section of FIG. 4, each housing 108 encloses, in a fluid-tight manner, a power source 120 electrically connected to a motor 122, to a circuit board 124, and to the stimulator 116. A first driver 130 is operatively connected to each motor 122 for cranial to caudal adjustments of the device 100. The first driver 130 is linearly translatable by linkages 134 operatively connected to the motor 122 within its housing 108 as shown in FIG. 3. The linkages 134 will be fluid-proof, heat-resistant and acid-resistant and thus able to withstand the conditions found within the oral cavity of a user.

With reference to FIGS. 2 and 3, the maxillary piece 102 is shown, which has a second teeth covering 107 and has a housing 109 proximate each of a left molar portion 111 and a right molar portion 113. Referring to the partial cross-sectional view of FIG. 3, each housing 109 encloses a power source 121 electrically connected to a motor 123 and to a circuit board 125. A second driver 132 is operatively connected to each motor 123 for anterior to posterior adjustments of the device 100. The second driver 132 is linearly translatable by linkages 135 operatively connected to the motor 123 within its housing 109.

In all embodiments, the housings 108 and 109 may be fixedly attached to the respective teeth covering, integral therewith, or removable attachable thereto. When removable attachable, the housings 108, 109 may be slid over a molar portion of the teeth covering, have a snap fit thereto, an interference fit thereto, may be a two-piece compartment that snaps together over a predetermined location of the teeth covering, may be three-dimensionally printed to cover or fit over a portion of the teeth covering. In all embodiments, while the teeth coverings 106, 107 are shown as full coverings for all teeth in the mandible and all teeth in the maxilla, the teeth coverings are not limited thereto. Instead, each teeth covering may be a partial cover for one or more teeth, as such, the mandibular piece 104 may be a two-part configuration having a left and a right portion each with a housing 108 and the maxillary piece 102 may be a two-part configuration having a left and a right portion each with a housing 109.

In all embodiments herein, each housing 108, 109 is described herein as positioned proximate a molar portion of a teeth covering, but is not limited to any particular size, i.e., the number of teeth to which it is associated. Each housing may be associated with one tooth region, a two-tooth region, a three-tooth region, or whatever number of teeth is needed to accommodate the size and position of the housing and its stimulator protrusion.

Figure 6:
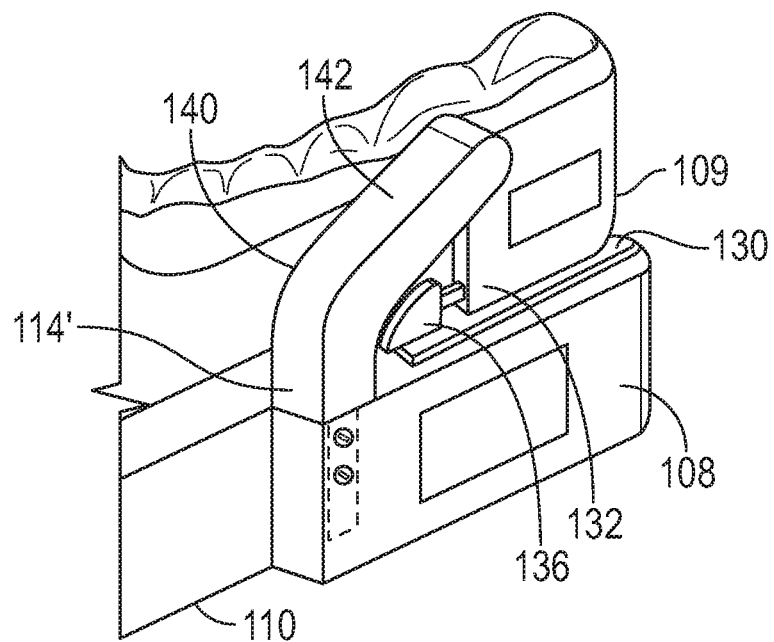
FIG. 6 is an enlarged view of the left movement mechanism of the mandibular lingual repositioning device of FIG. 1.
Figure 7:
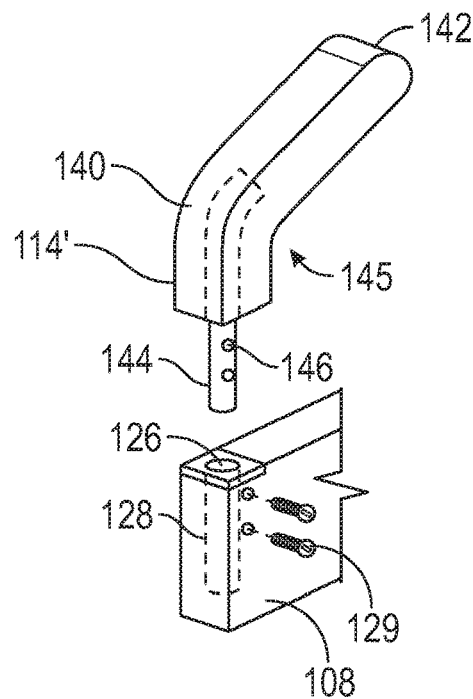
FIG. 7 is an enlarged view of an alternate embodiment of the left movement mechanism of the mandibular lingual repositioning device.

Referring to FIGS. 1, 3, and 4, the protrusive flange 114 of the mandibular piece 104 is an elongate flange that is releasably, removably attached to or may be integral with the housing 108. A releasably, removably attachable protrusive flange 114 is shown in FIGS. 6 and 7 to accommodate an interchangeability of protrusive flanges 114 of different shapes and sizes to provide the best fit for the user's mouth. In the embodiment of FIG. 1, the protrusive flanges 114 are generally an elongate linear flange protruding cranially from each of the housing 108.

Turning now to FIGS. 6 and 7, the protrusive flange 114' is releasably attachable to the housing 108 of the mandibular piece 104. The protrusive flange terminates with a post 144 opposite a free end 142 thereof. The post 142 includes a releasably attachable feature 146, such as a snap fit feature, a friction fit feature, or threaded holes as shown in FIG. 7. The housing 108 defines a receptacle 126 shaped to receive the post 144. The receptacle 126 will have a releasably attachable mating feature 128 that mates with the releasably attachable feature 146 of the post 144. In FIG. 7, the releasably attachable mating feature 128 is a set of threaded holes and screws 129.

Figure 8:
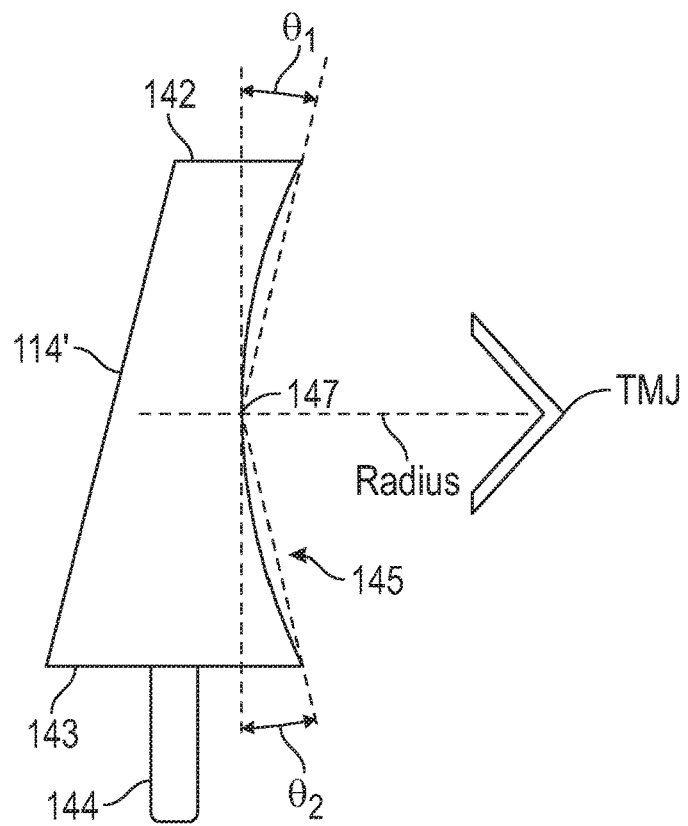
FIG. 8 is an enlarged side view of an embodiment of a protrusive flange.

As shown in FIGS. 6 and 7, the protrusive flange 114' can have a bend 140 on the anterior side of the flange, but this is not required. The new feature in this embodiment is that the posterior side 145 of the protrusive flange 114' is arcuately shaped as best shown in FIG. 8 as a concave surface, which mates with a driver 132 having a convex surface shaped to match the concavity of the posterior side 145. The midpoint 147, relative to being the middle or halfway point between the free end 142 and the opposing end 143, of the arcuately shaped posterior side 145 defines an arc of a circle having its center at the temporomandibular joint (TMJ) in this illustration and the free end 142 has a width that is smaller than a width of the opposing end 143 of the flange. The arc of the circle is one that defines $\theta_1$ as being any angle with the range of 12 degrees to 15 degrees in increments of whole degrees, half degree, or 0.2 degree increments. The angle of the arc $\theta_1$ defines the amount of protrusion of the mandible with each degree of mouth opening. The larger this angle $\theta_1$, the greater the protrusion with mouth opening. The larger the angle of mouth opening, the larger the protrusion of the mandible. The arcuate surface is customizable to provide a curvature that provides the best forward movement of the mandible for the user in relation to the individual user's mouth shape and size. Depending upon the shape and size of the user's mouth and jaws, the radius defining the point of the arc may be offset by moving this point up or down relative to the midpoint 147, which may change the widths of the free end 142 and the opposing end 143.

The advantage to the arcuately shaped side 145 of the protrusive flange 114' is that it will help protrude the mandible forward as the Temporo-Mandibular joint (TMJ) relaxes and the mouth falls open during sleep, wake or any other transitional state of the human mind (such as various Parasomnia create) thus allowing gradual smooth arcuate incremental forward mandibular movement to occur as concave surface 145 of protrusive flange 114' smoothly glides against convex surface 136 of driver 132'. The maximum protrusive distance (MPD) for anterior movement of the mandible is in a range of 6 mm to 10 mm. Typically, the first 13 degrees of rotation of the mandible about the TMJ during natural, un-aided spontaneous mouth opening does not move the mandible anteriorly, i.e., this rotation does not change or open the airway. Drivers 130, 132 will actively coordinate simultaneous desired amount of vertical and protrusive movements of the mandible (controlled by controller 200, described in more detail below) during this first 13 degrees of mouth opening while the arcuate opposing gliding movements of concave surface 145 of protrusive flange 114' smoothly against convex surface 136 of driver 132' surfaces will passively create mild forward movement of the mandible. Driver 132 will ensure constant contact between surfaces 145 and 136 while driver 130 will adjust height of oral cavity and thus increase oral cavity volume while simultaneously stiffening the soft palate and Uvula. This entire process will work in synergy (keeping the person's sleep undisturbed) to increase cross-sectional area of upper airway and increase the cubic volume of the oral cavity which in turn allows 150L/R (through the controller 200) in 116 to appropriately incrementally protrude the base of tongue forward into the increased oral cavity volume utilizing electric stimulation of the tongue nerves and muscles (details described elsewhere in this document), further increasing the cross-sectional area of the upper airway (the tongue forms the anterior wall of the upper airway).

In the natural state, the mandible must rotate beyond this initial 13 degrees, typically through another 7 to 13 degrees to have an effect on the airway size. In an example, where the arcuately shaped side 145 is based on a 15 degree jaw rotation (end to end) curvature, i.e., $\theta_1$ and $\theta_2$ are 15 degrees each or they may be any combination of two different angles that add up to 30 degrees. The approximate midpoint 147 of the arc 145 is the point at which transition between angle of $\theta_2$ and $\theta_1$ occurs and is approximately the point at which the mandible (mouth) is expected to have opened or rotated to the first 13 degrees (12 to 15 degree range). Total theta at the point of transition $147=180-(\theta_1+\theta_2)$. Surface 136 of driver 132 should align with the lower part of surface 145 closer to 143 when the mouth is completely closed (Centric Occlusion CO with a Centric Relation CR between mandibular and maxillary incisor teeth). Angle of $\theta_2$ can be different from angle of $\theta_1$, i.e., the arc may or may not be one fixed radius from TMJ. Each of the $\theta_1$ and $\theta_2$ should remain between the ranges of 12-15 degrees each although both $\theta_1$ or $\theta_2$ or both could be zero degrees each (0-15 degrees each). These angles could exceed 15 degrees each based on individual needs of the user/patient. Total of $(\theta_1+\theta_2)$ will ordinarily be between 24-30 degrees but could be 0-30 degrees or greater. Theta at point of transition 147 is $(180-(\theta_1+\theta_2))$ =150 to 180 degrees unless angles of $\theta_1$ or $\theta_2$ exceeded 15 degrees. A $\theta$ of 0 degrees will essentially create a straight vertical posterior surface 145 and would require a similar angle for surface 136. An angle of 180 would produce incremental forward protrusive movement of the mandible throughout the entire range of mandibular rotation (CR/CO to MMO) during mouth opening.

$\theta_2$ is primarily useful to control neutral mandibular protrusion during the initial 13 degrees of mandibular rotation (although protrusive flange can protrude the mandible when using MRD with motorized protrusive flange option) but can be adjusted to produce protrusive movement (the more $\theta_2$ is, the less the radius of mandibular incisor to TMJ, the less protrusion of the mandible during early rotation or mouth opening and the less $\theta_2$ is the more protrusion with each degree of mandibular rotation). On the other hand, $\theta_1$ is used to create the majority of the forward mandibular protrusion during the remainder of the mandibular rotation or mouth opening all the way to MMO (Maximum mouth opening).

Resistance to mouth opening will also occur during this part of mandibular rotation due to the resistance from stretching the muscles of the TMJ as the mandible incrementally protrudes with every additional degree of mandibular rotation. Increasing $\theta_1$ will cause even more protrusion of mandible and thus also cause incremental resistance to mouth opening created by forward jaw movement. Essentially, if the desired outcome is to keep the mouth closed or barely open (CR/CO position), one could use only $\theta_1$ and remove $\theta_2$ altogether. This would require an arcuate or non-arcuate straight posterior surface 145 with $\theta_1$ of 0-15 degrees from the vertical axis starting at base 143 all the way up to 142 as shown in FIG. 6 and FIG. 7 with a corresponding surface 136 that is straight non-arcuate surface with a corresponding angle $90+\theta_1$ or a corresponding arcuate surface that leans back as shown in FIG. 6 or combination of arcuate and non-arcuate surfaces such as shown in FIG. 6. Under these circumstances, greater the $\theta_1$ greater the protrusion of the mandible with the least amount of mandibular rotation or mouth opening (mm of protrusion for each degree of mandibular rotation) and thus also ensure the highest resistance to mandibular rotation and mouth opening to match the needs of the user/patient. In an example, where the arcuately shaped side 145 is customized with $\theta_1$ and $\theta_2$ of 15 degrees each as well (total theta=180−30=150) for the sake of simplicity of driving home the point, a mandibular rotation or mouth opening of about 20 degrees will protrude the jaw anteriorly about 5 mm and a mandibular rotation of about 24 degrees will protrude the jaw anteriorly about 11 mm. Since the MPD (Maximum Protrusive Distance with range of 6-10 mm) typically has an absolute maximum of 10 mm, 11 mm is nearly impossible for most people and thus the mechanics of the device create the environment where the mouth will not open to MMO (Maximum mouth opening) of 24 degrees.

The releasably attachable features of the flange 114' accommodates the interchangeability of protrusive flanges 114 of different shapes and sizes to provide the best fit for the user's mouth.

Referring back to FIGS. 1 and 4, at least one stimulator 116, but preferably both stimulators 116, include a first sensor 150L/R and/or a second sensor 152L/R, but preferably both sensors. 150L and 152L stands for the left side of the user and 150R and 152R stands for the right side of the user. The sensors 150L/R and 152L/R may be selected from a variety of sensors to create which every combination is the most likely to be useful in diagnosing or treating the user. The sensors are selected form the group consisting of a pulse oximetry sensor, a vibration sensor, an airflow sensor, a pH sensor, a combination pulse oximetry/vibration and airflow sensor, an EKG sensor, a pulse transit time (PTT) sensor, an ultrasound sensor (echocardiography), an electro-oculogram sensor, a temperature sensor, a body position or jaw position sensor (such as a potentiometer), an electromyogram sensor, a hygrometer sensor, and a microphone or sound recording sensor. In one embodiment the first sensor is a combination pulse oximetry/vibration and airflow sensor and the second sensor is a pH sensor. In another embodiment, the first sensor is a pulse oximetry sensor and the second sensor is a vibration and airflow sensor. Any number of combinations of the sensors listed above is possible and can best be selected by a medical professional based on data relative to the pre-selected end user.

The stimulator 116 may also be accompanied by a sensor or sensors that can record EEG (electro-encephalogram), EOG (electro-oculogram), electromyogram (EMG) for the tongue muscles and NC (Nerve conduction) data from the nerves of the tongue, pharynx and muscles of mastication (jaw muscles) and phonation (speech). These sensors may transmit these data to the controller 200 (described in more detail below) through variety of industry standard wireless protocols that are currently in use for wireless EMG, NC and EEG recordings in other skin surface applications in neurology and sleep laboratories. Data from such sensors will be useful for detection of various medical diseases as it will be computed in time-synchronized manner by the controller 200 and cloud based servers in system 300 described in more detail below and will help to determine cause-effect of many medical diseases. The sensors will also provide feedback to controller 200 to gauge effectiveness of electric stimulation of the tongue or forward movement of the tongue and mandible and thus allowing the controller to make fine adjustments to all components of the system.

The length L of each stimulator 116 will be pre-selected to fit the user's mouth and tongue, in particular for adequate contact with the base of the tongue during sleep. Each stimulator 116 has a single or dual electrode 154 connected to the power source 120 and generates an electrical impulse that travels through the electrode to one or more of the lingual muscles of the tongue identified above, which contracts the lingual muscle(s) to create a forward movement of the tongue. The forward movement of the tongue increases the cross-sectional open airway diameter in transvers, vertical and antero-posterior dimensions, thus increasing the aggregate volume of open airway and exponentially reducing air-flow resistance. The power source for the single or dual electrode can be a direct current (DC) power source or may employ any other technology such as electro-magnetic energy, photon energy among other forms of energy. The electrical impulses' power source will be in volts or microvolts and the current, likely in milli-Amps (usually 2-6 mA), will be pre-selected on a per patient basis. The power, current, and capacity will typically be within a range suitable for effective performance of mated hardware and safe for use with cardiac pacemakers, defibrillators, deep brain stimulators, or spinal cord stimulators.

The forward movement of the mandible (protrusion) is performed by lateral pterygoids, medial pterygoids and masseter muscles. These are stimulated by the mandibular branch of the trigeminal nerve. The neuronal firing rate drops during sleep relaxing these muscles causing the jaw to fall back (retrusion) and thus allowing the tongue to fall back (retro-glossal movement) into the airway as well creating a narrow airway which is the cause of obstructive sleep apnea, oxygen desaturation, elevated blood-pressure, cardiac arrhythmia, disruption in sleep and nocturnal acid reflux. The transverse stimulator 116 can specifically target these muscle groups and their distributing nerve and stimulate and sense electrical activity of these various muscles individually or together inside the oral cavity.

Also, the stimulators 116 can stimulate selected muscles to improve their strength. This can be a training or a retraining exercise, for example, after a stroke (swallowing difficulty or speech difficulty) or for children with speech pathologies. If sensors are present in the stimulators 116, the sensors can provide data to the controller station 200 and the system 300 of FIG. 11 to determine which muscle and/or muscle group needs attention. Thus, the shape of exterior surface/housing of the stimulators 116 are shaped and sized to direct each and every sensor, stimulator or combination thereof to the appropriate location inside the oral cavity.

The pulse oximetry sensor 150 is positioned in one or both stimulators 116 at a position enabling direct contact with the base of the tongue from which data will be collected. The position of the pulse oximetry sensor 150 is generally antero-superiorly positioned for measuring pulse-oximetry through the blood-flow of the tongue. The vibration and airflow sensor 152 is positioned in one or both stimulators 116 at a position suitable for airflow measurements, which can indicate when there is a restriction of airflow, and vibration measurements (sub-sonic and sonic) that are an indication of inaudible and audible snores. The vibration and airflow sensor 152 faces posteriorly to measure snores and airflow resistance/pressure from the airway.

The power source 120, 121 in all embodiments may be a rechargeable battery. In one embodiment, the rechargeable battery is one or more micro-lithium ion batteries in each housing 108, 109. Solar/light charging energy source that can be recharged by ambient lighting (used in the watch maker industry) or solar power may also be considered for a rechargeable source of energy. The rechargeable battery may have a maximum discharge milli-amperage creating a mechanical mandibular protrusion or retrusion ranging between 1-10 mm in linear dimensions for the movement of the drivers 130, 132.

As seen in FIGS. 1 and 2, each housing 108, 109 of the mandibular and maxillary pieces, respectfully, include a charging member 118, 119, such as a charging plate, in an exterior surface thereof. In the figures, the charging plate is in a lateral side of the housing 108, 109, but is not limited thereto.

As best seen in FIG. 3, the first driver 130 may be a flat plate connected to the motor 122 by the linkages 134.

The motor 122, 123 in all embodiments may be a single or dual piezoelectric motor having a linearly movable linkage(s). Micro motors based on piezo electric materials are commercially available from Piezo Motor, a company headquartered in Sweden and may be modified as needed for use in the disclosed devices. The motor 122, 123 may include a position sensor.

As best seen in FIGS. 3 and 6, the maxillary piece 102 sits on the mandibular piece 104 with the first driver 130 operatively engaged with the maxillary piece 102 and the second driver 132 operatively engaged with the protrusive flange 114, 114' of the mandibular piece 104. Each of the drivers 130, 132 can move the jaws in increments of 0.1 mm up to 2 mm with each movement with a maximum of 12 mm in the respective direction. The protrusive flange 114, 114' is moveable by the second driver 132 in a range from 0.1 mm to 11 mm and the first driver 130 can lift the maxillary portion in a range from 0.1 mm to 12 mm. Referring again to FIG. 6, the second driver 132 has a head 136 that is shaped to fit the shape of the posterior side 145 of the protrusive flange 114'. The head 136 has a convexly-shaped anterior side to press against the posterior side 145 of the protrusive flange 114'.

Figure 9:
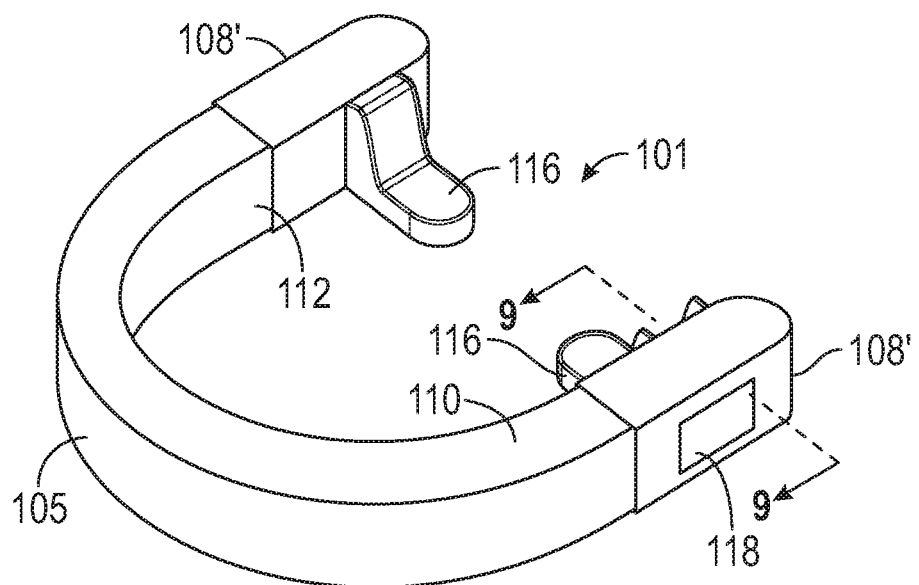
FIG. 9 is a side, perspective view of an embodiment of a mandibular device having at least a stimulator electrode therein.

Turning now to FIG. 9, a mandibular device 101 is illustrated that has just the stimulator 116 and a mandibular teeth covering 105. As such, the maxillary piece can comprise a teeth covering 107 as shown in FIG. 2 without the housings 109 or it can be absent, i.e., the user can just have the mandibular device 101 in their mouth during use. Dual housings 108' are present with one each proximate a left molar portion 110 and a right molar portion 112. A stimulator 116 extends from each housing 108' toward the tongue at a position to lie under the tongue in contact with lingual muscles, in particular the Genioglossus (GG), the Geniohyoid (GH), sub-mentalis (SM), and Glossopharyngeal (GP). Each housing 108' includes a charging feature 118 for recharging any battery(ies) housed therein, as described above.

Figure 10:
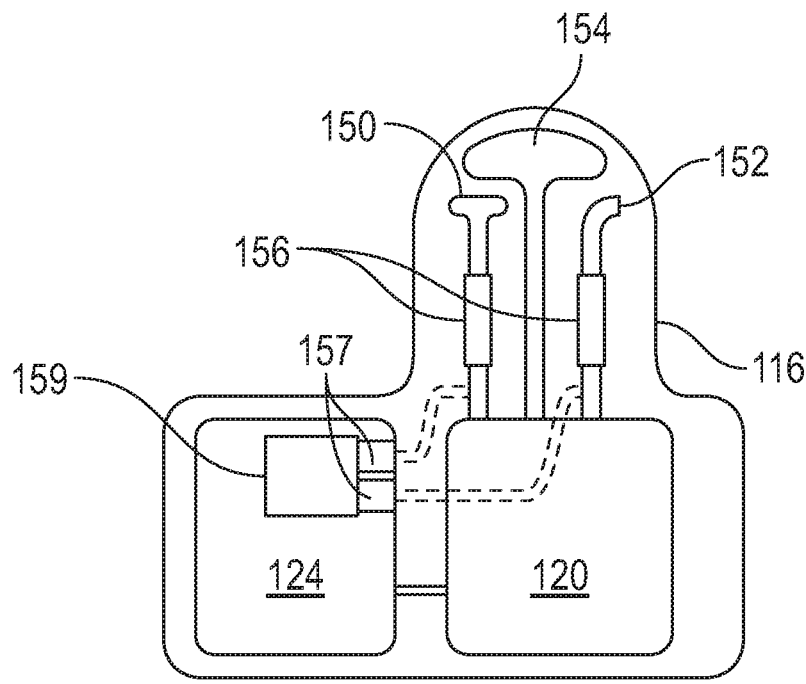
FIG. 10 is an enlarged cross-sectional view of the mandibular device along line 9-9 in FIG. 9.

Referring now to the cross-section of FIG. 10 through one of the stimulators 116, each stimulator 116 houses therein, in a fluid-tight manner, a first sensor 150, a second sensor 152, and a stimulator electrode 154. In FIG. 10, the first sensor 150, the second sensor 152, and the stimulator electrode 154 are each electrically connected to the power source 120 within housing 108'. The electrical connections may be direct connections to the power source 120, which may be accomplished by a plug-n-play electrical connector 156, or, as represented by the dashed lines, may be accomplished by a plug-in style connector 157 to the microprocessor 159 and thereby to the power source.

In one embodiment, the first sensor 150 is a pulse oxygen sensor continually measuring oxygen data at the base of the tongue and the second sensor 152 is a vibration/air flow sensor measuring snoring, turbulent flow, and vibrations from inside the user's mouth. As noted above with respect to FIG. 4, multiple other sensors and sensor combinations are possible that will provide data to the microprocessor 159. The circuit board 124 within the housing 108' is in operative connection to the power source to be powered and to control activation of the stimulator electrode 154 in response to data received by the circuit board 124, more particularly, the microprocessor 159, from the first sensor 150 and/or the second sensor 152. As discussed the microprocessor 159 receives the sensor data, processes the sensor data, and determines whether the stimulator electrode 154 needs activated.

Each of the stimulators 116 may include a pH electrode too. The pH electrode will measure the acidity at the back of the tongue, which if too high is an indication of chronic high acid reflux.

Figure 5:
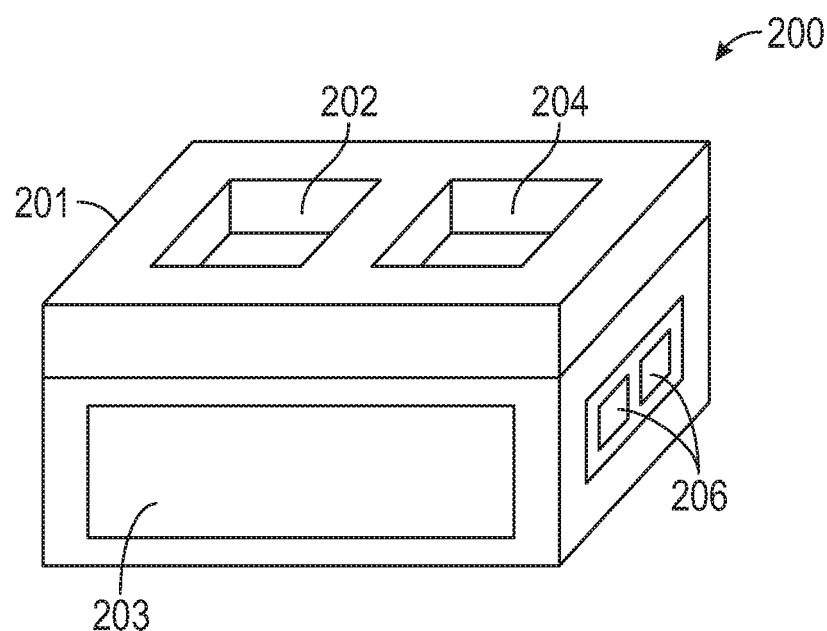
FIG. 5 is front, perspective view of a controller station for use with the devices disclosed herein.
Figure 11:
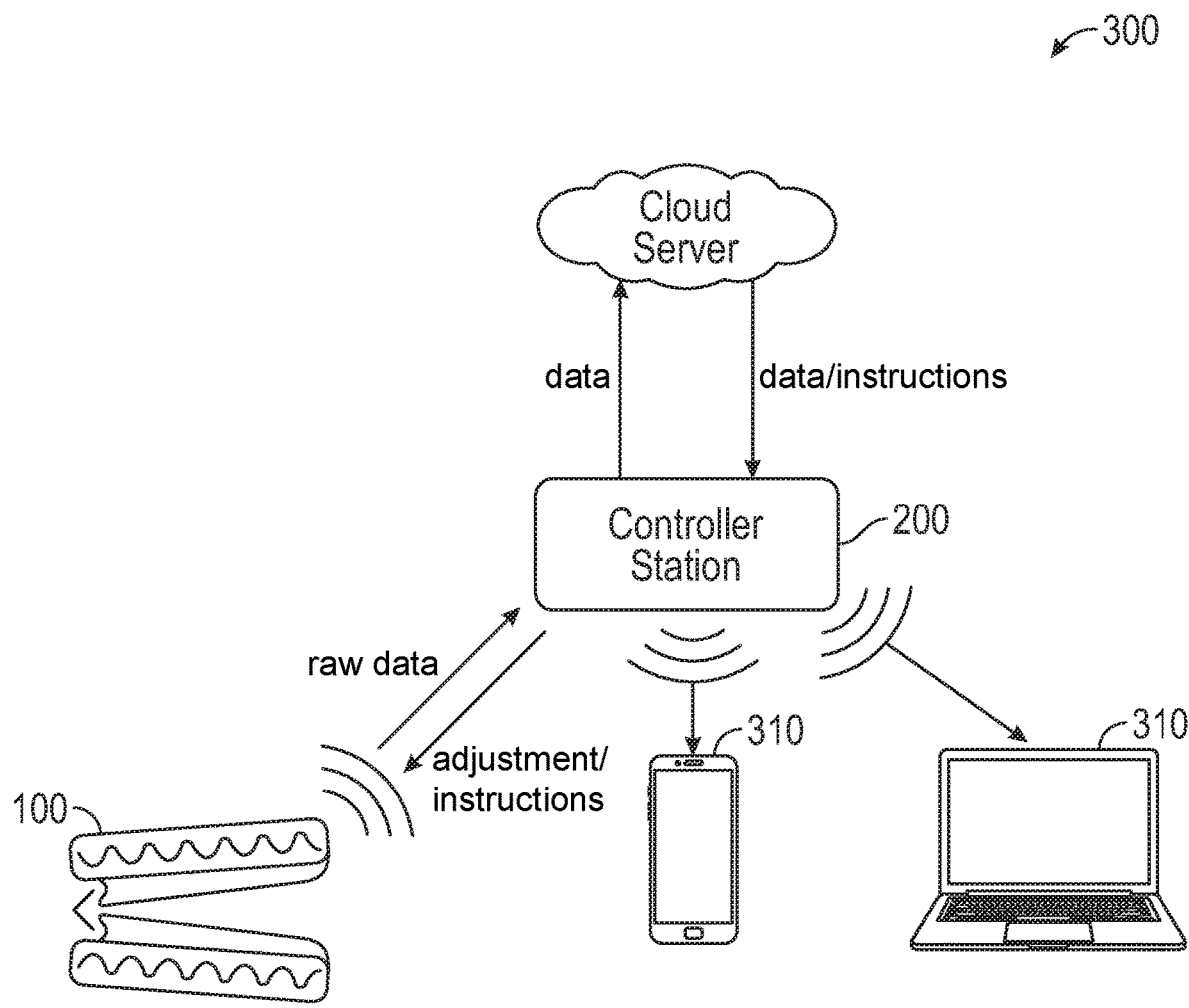
FIG. 11 is a schematic illustration of a system in operative communication with the MRLD of FIG. 1 or the mandibular device of FIG. 8.
Figure 11:
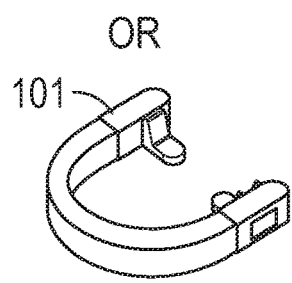

Turning now to FIGS. 5 and 11, a controller station 200 is illustrated for operatively controlling any of the mandibular lingual repositioning devices 100, 101 described above, which together define a system 300 schematically illustrated in FIG. 11. The controller station 200 has a housing 201 defining a first charging unit 202 for receipt of the maxillary piece 102 and a second charging unit 204 for receipt of the mandibular piece 104. The first and second charging units 202, 204 may be receptacles defined in a surface of the housing 201. In another embodiment, the first and second charging units 202, 204 may be generally flat plates. The housing 201 has a display screen 203 for displaying information to a user and one or more ports 206 for connecting the charging station to power, other devices, and/or the internet. Alternately, instead of ports 206, the housing 201 can enclose wireless communication technology for other devices 310, for example, but not limited thereto, a printer, speakers, tablets, laptops, cellular phones, smart watches, and other cloud-based devices. The controller station 200 may include sensors to record ambient room conditions, such as light, temperature, humidity, noise/sound, etc. The controller station 200 optionally is battery powered and may include a rechargeable battery. The controller station 200 may be portable.

Alternately, rather than having the first and second charging units 202, 204 integrated into the controlling station 200, a separate charging station (not shown) having a first and second charging unit is possible. The charging station may be portable.

When the charging station is separate from the controller station 200, the controller station may be incorporated into a hand-held smart device and such a smart device would share blue tooth, WIFI, Video, audio and communication capability with sensors. In one embodiment, the controller can be a proprietary software program for use with or an App (software application) having full functionality to function like the controller station 200. System 300 and controller station 200 in all its embodiments will be HIPPA and HITECH compliant for purpose of medical privacy. Interface with the wide variety of electronic health formats (EHR) would allow system 300 and controller station 200 and its operated systems to be available for real-time data download and upload, active health care worker involvement in user's health care needs and would permit the health care worker to operate and alter any treatment and access and interpret diagnostic information provided by the system. As such controller station 200 and system 300 would allow newer formats of health care provisions such as tele-medicine and others yet to be defined. System 300 may be integrated into a full-function health care software-hardware system for patient assessments (such as telemedicine), tests, treatments and medications.

The controller station 200 encloses a circuit board having a microprocessor, including memory (non-transitory computer readable media) in which is stored firmware and learning algorithms, having a receiver of electronic communications, and having a transmitter of electronic communications, including wireless communication capabilities to electronically communicate with at least the MLRD 100, 101 for real-time communications with the sensors on board the MLRD. The MLRD 100, 101 has microprocessors on-board with a transmitter to transmit raw data from all sensors, stimulators and pressure pellets exemplified by the pulse oximetry sensor, the vibration and airflow sensor, lingual stimulator, lateral pterygoid stimulator, medial pterygoid or masseter stimulator, EKG sensor, sub-lingual nitroglycerine pellet discharge, etc. to the controller station 200 in real-time aided by system 300 for processing into executional commands exemplified by movements of the first driver and/or the second driver and activation of the stimulator for tandem or synchronized movements and activation thereof, i.e., simultaneous, independent, or sequential activation of the motors and the stimulator, training of muscles of speech or swallowing including the sequence of movement and strength and duration of current or release of a medication for sublingual or aerosolized use. The controller station 200 can simultaneously transmits the instructions to the MLRD 100, 101 microprocessors in each housing 108, 109, 108' which implement the instructions, exemplified by synchronizing the cranial to caudal adjustments, the anterior to posterior adjustments, and activation of the stimulator etc. The MLRD may also operate as a stand-alone mandibular protrusive and vertical advancement device or as a stand-alone lingual/pterygoid stimulator device or a timed-medication release device as preferred by treating health care provider.

The circuit board of the controller station 200 receives data from the pulse oximetry sensor and/or the vibration and air sensor and activates the motors and the stimulator as needed after a pre-selected number of breaths of the user. The firmware and algorithms, including learning algorithms as well as standard algorithms, stored in the memory of the circuit board may define the pre-selected number of breaths to be every breath, every other breath, every five breaths, or an absence of breath(s). Since the movements of the MLRD 100, 101 are done in real-time, the airway of the user can be opened without disturbing the sleep of the user.

The controller station 200 has a microprocessor configured to process the data and instruct the MLRD 100, 101. However, the controller station 200 can communication with a server, such as a cloud server, for further processing if desired, or for additional memory storage and/or communication of the data to authorized healthcare providers and/or sleep analysis experts, etc. and/or communicate with a database of said person. This intercommunication of databases can create therapeutic interventions and diagnostic testing of a user while at home or across continents. This system 300 enables an authorized healthcare provider to monitor and record patient data in real time, learn the patient, and alter the patient's treatment in real-time. The communications to and from the server can be through a wired or a wireless connection.

The server can also send commands, configuration data, software updates, and the like to the controller station 200 in whatever form it may exist. The configuration data may include, but is not limited to, configuration parameters for the system 300, configuration parameters for a particular user, and/or notifications, feedback, instructions, or alerts for the user.

The system 300, in addition to the MLRD 100, 101 can wirelessly communicate with additional sensors connected to the user to provide a broader data set for a more complete picture of the user's physiology. For example, electrocardiogram (EKG), electromyography (EMG), electrooculography (EOG), electroencephalography (EEG) sensors, echocardiography, blood pressure monitoring systems, and sensors sensing environmental conditions, such as temperature, ambient light, and humidity. The system may include a camera for video recording through the controller station 200 to evidence any nocturnal seizures, sleep-walking, other movement or violent disorders during sleep.

In operation, data from the sensors on the MLRD 100, 101, such as oxygen measurements and pulse data, is sent to the controller station 200 to be processed by the microprocessor to determine how much movement of the protrusive flange by activation of the second driver is needed, how much movement of the first driver is needed to separate the jaws of the user, and if and when to stimulate the transverse lingual muscle of the tongue to move the tongue forward. After some breaths, the controller station 200 may determine to stimulate the tongue and activate the second driver to move the mandibular piece, and hence the jaw of the user, forward (anterior) or backward (posterior) direction. In other instances, the controller station 200 may determine to stimulate the tongue and activate both the first driver and the second driver to separate the jaws and move the mandibular piece forward in order to adequately open the airway of the user.

The system 300 also creates three-dimensional images and videos of breathing, cardiac function, carotid blood flow data, eye-movements, jaw movements and brain EEG recordings for identification of medical conditions and interventions that may be useful to correct or treat those medical conditions.

A unique advantage of this system over any other existing systems is that the jaw and tongue can move synchronously, independently, or sequentially during sleep in real-time and in anticipation of impending airway closure and in a provision of a measured response to restriction of airflow as determined by the controller station 200 even before the airway has completely closed; thus, restoring unrestricted airflow even before the patient has completely stopped breathing. This system can see airway obstruction before it happens and will keep the airway constantly open in any body position or depth of sleep. This is a distinct advantage over CPAP/BIPAP or any other mechanical or electrical system that is commercially available in the market. In addition, there are distinct advantages just by the breadth of functionality that has been described above. Any discussions herein directed to the mandibular component, with respect to the controller station 200 and the system 300, are equally applicable to the maxillary component.

The controller station 200 includes learning algorithms in the memory of the microprocessor that learns a user's sleep patterns and other physiological events and functions during sleep and wake, pathological events and activities during wake and sleep from the data collected over time and creates a "best response" for the simultaneous, independent, or sequential responses exemplified by tensing of the soft palate or Uvula, release of medication or stimulation of the stimulator and activation of the first and second drivers to open the airway or to train muscles of speech, and to synchronize these best responses such as exemplified by certain jaw movements that are associated with particular phases of respiration. The activation of the first and second drivers 130, 132 not only includes advancements, but also retractions of the first and second drivers 130, 132 to relax the jaws in between necessary advancements to open the airway to avoid potential TMJ problems.

The controller station 200, in the memory of the microprocessor, may include a pre-programmed range for the movements of the first and second drivers 130, 132 based on sleep study data for the user conducted by an authorized healthcare provider. The pre-programmed range can be used by the controller station 200 in a stand-alone or auto servo mode. The pre-programmed range may be determined by simple or multiple linear regression models that employ data from inputs and from previous experiences, which the controller station 200 will be able to forecast ranges for the amount and direction of movements of the drivers 132, 134 and the amount or timing of energy discharge through the transverse stimulator(s). The controller station 200, in the memory of the microprocessor, may include data from tests previously performed on the user and/or the output of algorithms to set the MLRD 100, 101 each day for use just prior to sleep.

The controller station 200 can operate based on a stand-alone function or a servo function. In the standalone function, the controller station 200 operates the MLDR 100, 101 based on set parameters such as are exemplified by the movement of the drivers, such as repetitive equal advancement and retraction of the mandible that are not based on active feedback. For example, a set 2 mm movement anteriorly of the mandible during each breath and a 2 mm posterior movement of the mandible after each breath, with a fixed amount of energy discharge to the electrode of the stimulator. The set parameters for the standalone function may be based on data collected from the specific user or may be based on a peer group of like sleep attributes.

In the servo function, the controller station 200 interactively controls the MLRD 100, 101 during sleep or wake, at home or elsewhere, based on the data collected from the sensors on-board the MLRD in a feedback loop and based on data available from the server. During operation, the continual feedback loop allows incrementally accurate interventions followed by listening to observational inputs exemplified by airflow measurements, video recordings, pulse-oximetry, doppler flow in carotids or advancement of mandible and followed by more interventions exemplified by protrusive or vertical adjustments based on real-time data even after a previous advancement or incremental increase in energy to stimulate the tongue. The changes to the advancement or application of energy to the stimulator will be capable of producing positive and negative changes regarding movement of the mandible and tongue. For example, the energy applied to the stimulator may be reduced relative to the prior application of energy discharge if the previous discharge of energy caused teeth grinding or cough. In another example, the protrusive movement of the jaw may be reversed if the previous protrusion advancement caused a deleterious change in any of the monitored physiological parameters. In another example training of muscles of swallowing would be altered upon observing retrograde movement of food or appearance of cough or gag.

Also, in the servo function, data from all sources, server, MLRD, and any other sensors attached to the user that are communicating with the controller station 200, are continuously processed through algorithms that are stored in the memory of the controller or stored in the server. Examples of other sensors includes, but is not limited to, wireless pulse-transit time sensors, and wireless EKG sensor. These two additional sensors would be utilized in addition to the MLRD to diagnose and treat sleep-induced hypertension and/or cardiac arrhythmia such as lack of oxygen to the heart, especially by collecting time synchronized data from the EKG sensor and the pulse oximeter sensor. For example, the server may include data related to sleep attributes and alcohol consumption to make adjustments for the user during sleep after drinking alcohol. For example, it may require a change in current applied to the stimulators 116 after alcohol consumption to effectively stimulate the lingual muscles. The same may be true of a user taking certain medications, especially those that depress brain function. As another example, the server may include data on myriad patients correlating sleep attributes to weight loss. As such, if the user loses 5 or 10 pounds, data from the server can be considered in the algorithm determining how much movement of the jaws is needed and/or whether to stimulate the tongue.

The system 300 may be used to treat many medical diseases, including but not limited to any type of sleep apnea, bruxism, sleep related GERD, sleep-induced hypertension, snoring, etc.

The system 300 may be used to diagnose any possible medical conditions related to sleep, including sleep apnea or other sleep disorders including sleep-induced hypertension, sleep-related cardiac arrhythmia, sleep related seizures, RLS and periodic limb movement disorders. Here, the MLRD 100 or 101 is placed in the user's mouth during a sleep period, such as at night, with the controller station 200 in a "test mode" in which the on-board sensors measure and monitor the user's physiological parameters mentioned above. The test mode is used for multiple sleep periods of over two to 30 days, based on a time period set by a medical professional. For example, the user may have the controller station in "test mode" for seven days. Then, the seven days of data is reviewed by the medical professional to determine whether the user has sleep apnea or any other sleep disorder, and if so, determines the parameters for the standalone mode, which are then stored in the controller station 200. The same system may be used even during the day and outside of the home of the user such as at place of work.

The system 300 may have a therapeutic mode, which implements the servo function. Here, the feedback loop is on for data from the on-board sensors, which is processed through an algorithm to determine the least amount of anterior and caudal movement to maintain an open airway and the least amount of energy discharge to stimulate the tongue and maintain an open airway and the order in which to take such actions, i.e., simultaneously, sequentially, or individually.

The device and system disclosed herein have numerous advantages, including artificial intelligence utilizing data collected by the MLRD during use to actively in real-time adjust the MLRD in response to the phases of respiration, degree of obstruction of the airway, snore sounds and vibrations and amount of hypoxemia present relative to each breath irrespective of the stage of sleep of the user. The system is capable of measuring a large number of cardiac, neurological and endocrine sensory inputs as described above exemplified by continuous non-invasive glucose, oxygen, blood pressure, pH monitoring, heart rhythm and temperature etc. The system is capable of photography for creating dental impressions, dentures or to diagnose gum disease etc. The system is capable of executing a large spectrum of functions such as mandible protrusion, administering sub-lingual insomnia medication like Intermezzio or cardiac medication like Nitroglycerine or training muscle groups for swallowing or speech. The system is capable of communicating with user, provider, EHR (Electronic Health Record) and pharmacy etc. This system is capable of determining restriction to airflow, increase in velocity of air and turbulence, decreasing levels of oxygen and increasing levels of heart rate, pH monitoring and any other physiological parameter that could be installed in the future with constant inputs of physiological parameters (unlike with CPAP machine or oral appliances that are available in the industry), such as those mentioned above. This collection and processing of data allows the system to actually make adjustments exemplified by the movement of the mandible and tongue prior to closure of the airway and hence will work as a preventative form of treatment for sleep apnea.

Age and gender specific physiology of the airway and the mouth during sleep are known to affect sleep and cause sleep disorders. The system 300 and 310 will collect data that will enable the development of algorithms that are age and gender specific, which can improve treatment outcomes for future users. System 300 and 310 has ability to create database of all physiological and pathological events measured in real-time and time synchronized with each other in its users and develop algorithms for normal and abnormal manifestations of disease states during wake and sleep and develop new cause-and-effect understanding of these events that have never been observed before. Recording and correlation of these phenomenon with sensors, especially during sleep would help understand conditions such as 'wake-up strokes' (occur during sleep) that account for 14% of all strokes and diagnose conditions like obstructive sleep apnea that occurs with almost 83% of cardiovascular disease, 58% of heart failure and 53% of atrial fibrillation, to name a few.

The system not only advances movement of the mandible (cranially and anteriorly), but enables a relaxed movement of the mandible (caudally and posteriorly), which allows the temporomandibular joint to relax periodically to prevent jaw discomfort, temporomandibular joint strain and destabilization, morning stiffness of said joint, and alteration of the user's bite.

The system 300 can also be used for users that snore, but who do not yet have sleep apnea. The inclusion of the vibration and airflow sensor enables the measurement of the intensity of snoring and can open the airway before the sub-sonic snore has become audible. The inclusion of stimulators of soft palate and uvula can reduce or eliminate snoring in users that do not have sleep apnea yet. Also, the system 300 can be used along with a CPAP machine and enable the CPAP machine to be used at a lower air pressure than a typical setting for user's that cannot tolerate CPAP machine at their typical air pressure.

It should be noted that the embodiments are not limited in their application or use to the details of construction and arrangement of parts and steps illustrated in the drawings and description. Features of the illustrative embodiments, constructions, and variants may be implemented or incorporated in other embodiments, constructions, variants, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Having described the invention in detail and by reference to preferred embodiments thereof, it will be apparent that modifications and variations are possible without departing from the scope of the invention which is defined in the appended claims.

What is claimed is:

1. A mandibular repositioning device comprising:
a mandibular piece having a first teeth covering having a protrusive flange extending cranially from each of a left molar portion and a right molar portion; and
a maxillary piece having a second teeth covering and having a second housing proximate to each of a second left molar portion and a second right molar portion, wherein each second housing of the maxillary piece encloses a power source electrically connected to a piezo-electric motor and to an on-board circuit board and has a driver operatively connected to the piezo-electric motor for anterior and posterior movements of the driver, thereby operatively, actively driving anterior movement of the mandibular piece and operatively, actively moving the driver posteriorly;
wherein the maxillary piece sits on the mandibular piece with the driver operatively engaged with the protrusive flange of the mandibular piece;
wherein the protrusive flange has a concavely-shaped posterior surface, the driver has a convexly-shaped head shaped to match the concavely-shaped posterior surface of the protrusive flange, and as the mandibular piece moves downward with jaw opening the concavely-shaped posterior surface of the protrusive flange of the mandibular piece slides against the convexly-shaped head for gradual arcuate incremental forward mandibular movement, which passively increases the cross-sectional area of the user's upper airway.

2. The device as claimed in claim 1, wherein the protrusive flange is releasably attachable to the housing of the mandibular piece, thereby being replaceable with another protrusive flange.

3. The device as claimed in claim 1, wherein each power source is a rechargeable battery and each housing has a charging member in an exterior surface thereof.

4. The device as claimed in claim 1, wherein the on-board circuit board includes a receiver, a transmitter, and a microprocessor having instructions to activate the motors simultaneously to linearly translate the driver.

5. The device as claimed in claim 1, wherein the protrusive flange has a midpoint between opposing ends, and the concavely-shaped posterior surface thereof is an arc of a circle having its center configured to be at a temporomandibular joint of a user and a radius terminating at the midpoint or offset above or below the midpoint and defines an angle $\theta_1$ relative to a free end of the opposing ends and defines an angle $\theta_2$ relative to an opposing end.

6. The device as claimed in claim 5, wherein $\theta_1$ and $\theta_2$ are in a range of 12 to 15 degrees.

7. The device as claimed in claim 5, wherein $\theta_1$ and $\theta_2$ are a combination of angle values that sum to 30 degrees.

8. The device as claimed in claim 7, wherein $\theta_2$ is different than $\theta_1$.

9. The device as claimed in claim 7, where $\theta_1$ is greater than $\theta_2$.

10. A mandibular repositioning device comprising:
a mandibular piece having a first teeth covering and having a housing proximate each of a left molar portion and a right molar portion, wherein each housing encloses a power source electrically connected to first on-board circuit board and to a motor, and a first driver oriented to move caudally and cranially, and comprising a protrusive flange extending cranially from each housing;
a maxillary piece having a second teeth covering; a second driver mated to a posterior surface of each of the protrusive flange, and a second housing proximate each second driver, wherein each second housing of the maxillary piece encloses a power source electrically connected to a motor and to a second on-board circuit board and has one of the second drivers operatively connected to the motor and in operative engagement with the protrusive flange for anterior and posterior movements of the mandibular piece; and
a sensor in either or both of the mandibular piece and the maxillary piece, each sensor being in operative communication with at least one of the on-board circuit boards;
wherein the maxillary piece sits on the mandibular piece with the first driver operatively engaged with the maxillary piece to open or close the mouth of the user;
wherein the posterior surface of each protrusive flange is a concavely-shaped and configured to slide against a convexly-shaped head of the second driver as the mandibular piece moves downward with jaw opening, which moves the mandibular piece forward and increases the cross-sectional area of the user's upper airway;
wherein the first on-board circuit boards are configured to receive instructions to incrementally open or close the mouth of the user by activating each of the first drivers based on data from each sensor collected in real-time regarding the user, thereby affecting dynamic anterior advancement simultaneously therewith according to the curvature of the concavely-shaped posterior surface of the protrusive flange in real-time during the user's sleep, and the second on-board circuit boards are configured to receive instructions to move the second driver anteriorly or posteriorly by activating each of the second drivers based on data from each sensor collected in real-time regarding the user, thereby providing an additive or subtractive effect to the dynamic anterior advancement.

11. The device as claimed in claim 10, wherein the protrusive flange has a bend that orients the free end thereof generally toward the posterior and the second driver has a head shaped to fit the shape of the posterior side of the protrusive flange.

12. The device as claimed in claim 10, wherein the protrusive flange is releasably attachable to the housing of the mandibular piece, thereby being replaceable with another protrusive flange.

13. The device as claimed in claim 10, wherein each power source is a rechargeable battery and each housing has a charging member in an exterior surface thereof.

14. The device as claimed in claim 10, wherein the instructions are based on data from a health care software-hardware system.

15. A mandibular repositioning device comprising:
a mandibular piece having a first teeth covering and having a protrusive flange extending cranially from each housing of the mandibular piece; and
a maxillary piece having a second teeth covering and having a second housing proximate to each of a second left molar portion and a second right molar portion, wherein each second housing of the maxillary piece encloses a power source electrically connected to a motor and to an on-board circuit board and has a driver operatively connected to the motor for anterior and posterior movements of the mandibular piece;
wherein the maxillary piece sits on the mandibular piece with the driver operatively engaged with the protrusive flange of the mandibular piece;
wherein the protrusive flange has a concavely-shaped posterior surface configured to slide against a convexly-shaped head of the driver as the mandibular piece moves downward with jaw opening, which moves the mandibular piece forward and increases the cross-sectional area of the user's upper airway;
wherein the protrusive flange has a midpoint between opposing ends, and the concavely-shaped posterior surface thereof is an arc of a circle having its center configured to be at a temporomandibular joint of a user and a radius terminating at the midpoint or offset above or below the midpoint and defines an angle $\theta_1$ relative to a free end of the opposing ends and defines an angle $\theta_2$ relative to an opposing end.

16. The device as claimed in claim 15, wherein $\theta_1$ and $\theta_2$ are in a range of 12 to 15 degrees.

17. The device as claimed in claim 15, wherein $\theta_1$ and $\theta_2$ are a combination of angle values that sum to 30 degrees.

18. The device as claimed in claim 17, where $\theta_1$ is greater than $\theta_2$.

19. The device as claimed in claim 15, wherein the protrusive flange is releasably attachable to the housing of the mandibular piece, thereby being replaceable with another protrusive flange.

20. The device as claimed in claim 15, wherein each power source is a rechargeable battery and each housing has a charging member in an exterior surface thereof.

21. The device as claimed in claim 15, wherein the on-board circuit board includes a receiver, a transmitter, and a microprocessor having instructions to activate the motors simultaneously to linearly translate the driver.

* * * * *

UNITED STATES PATENT AND TRADEMARK OFFICE
CERTIFICATE OF CORRECTION

PATENT NO. : 11,484,435 B2
APPLICATION NO. : 16/784750
DATED : November 1, 2022
INVENTOR(S) : Ghuge It is certified that error appears in the above-identified patent and that said Letters Patent is hereby corrected as shown below:

In the Claims

Column 17, Line 9, Claim 10, "to first" should read --to a first--.

Column 17, Line 15, Claim 10, "covering;" should read --covering,--.

Signed and Sealed this
Twentieth Day of December, 2022

*Katherine Kelly Vidal*

Katherine Kelly Vidal
*Director of the United States Patent and Trademark Office*